US00PP33754P2

(12) United States Plant Patent
NeSmith

(10) Patent No.: US PP33,754 P2
(45) Date of Patent: Dec. 21, 2021

(54) SOUTHERN HIGHBUSH BLUEBERRY PLANT NAMED 'TH-1797'

(50) Latin Name: *Vaccinium corymbosum*
Varietal Denomination: TH-1797

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/216,943

(22) Filed: Mar. 30, 2021

(51) Int. Cl.
*A01H 6/36* (2018.01)
*A01H 5/08* (2018.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Thomas Horstemeyer LLP

(57) ABSTRACT

A new and distinct cultivar of *Vaccinium* plant named 'TH-1797', characterized by a combination of early season flowering and ripening, large berries with good color and flavor, high quality fruit production in conventional production areas, and a chilling requirement of about 200-300 hours below about 45° F.

6 Drawing Sheets

Botanical designation: *Vaccinium corymbosum.*
Cultivar denomination: 'TH-1797'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-1797'.

The new *Vaccinium corymbosum* 'TH-1797' was first identified in 2013 in Griffin, Ga. The new variety 'TH-1797' is early season, begins flowering and ripening slightly before other early varieties, has large berries with good color and flavor, and a chilling requirement of about 200-300 hours below about 45° F.

'TH-1797' is a product of a cross of 'TH-1120' X 'Suziblue' made by D. Scott NeSmith in 2010. 'TH-1120' is a non-patented breeding selection, and 'Suziblue' is a patented variety (U.S. Plant Pat. No. 21,167). The new blueberry plant variety 'TH-1797' has been tested in asexually propagated (by vegetative cuttings) plantings in Alapaha, Ga. since 2014 where it was established for testing and comparing to industry standards. Observations of the resulting 'TH-1797' progeny have shown that the unique features of this new *Vaccinium corymbosum* 'TH-1797' are stable and reproduced true to type in successive generations.

SUMMARY OF THE INVENTION

The new *Vaccinium* cultivar 'TH-1797' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-1797'. In combination, these traits set 'TH-1797' apart from all other existing varieties of southern highbush blueberry known to the inventors:

1. early flowering and ripening (before early varieties 'Suziblue' and 'Rebel' in South Georgia);
2. large fruit with good color and flavor as compared to 'Suziblue' and 'Rebel';
3. high quality fruit production in conventional production areas with frost protection; and
4. chilling requirement of about 200-300 hours below about 45° F. (based on comparison of flowering dates with those of known standard cultivars).

Comparison: Plants of the new *Vaccinium corymbosum* can be compared to other early season southern highbush blueberry cultivars 'Suziblue' (U.S. Plant Pat. No. 21,167) and 'Rebel' (U.S. Plant Pat. No. 18,138). The selection 'TH-1797' begins flowering and ripening slightly earlier than early varieties 'Suziblue' and 'Rebel' in South Georgia and has a similar flowering and harvest period. 'TH-1797' has large berries with good color and flavor as compared to 'Suziblue' and 'Rebel' at Alapaha (Table 1). No notable diseases or other pest problems have been observed for the new variety that are not also common for other varieties. The new variety is estimated to have a chilling requirement of about 200-300 hours, more or less, below about 45° F. (based on comparison of flowering dates with those of known standard cultivars) when produced under typical low to mid chill production regions. Studies suggest that 'TH-1797' produces high quality fruit when grown in conventional production areas, with frost protection advised for achieving acceptable yields due to its early flowering. Additional comparison data of 'TH-1797' with 'Suziblue' and 'Rebel' are presented in the table below.

TABLE 1

Plant and fruit ratings for 'TH-1797' and standards grown in Alapaha, GA. Data represents and average of data from 3 years (2016, 2019, and 2020).

| | 'Suziblue' | 'Rebel' | 'TH-1797' |
|---|---|---|---|
| Berry size | 8.0 | 7.6 | 8.2 |
| Berry scar | 7.0 | 7.2 | 7.8 |
| Berry color | 7.0 | 7.0 | 7.8 |
| Berry firmness | 7.3 | 7.2 | 7.5 |
| Berry flavor | 7.0 | 6.3 | 7.6 |
| Cropping | 8.5 | 7.0 | 6.5 |
| Plant vigor | 8.0 | 8.2 | 8.5 |
| Date of 50% flowering | Feb. 28 | Feb. 26 | Feb. 22 |
| Date of 50% ripening | May 7 | Apr. 27 | Apr. 24 |
| Fruit development period (days) | 69 | 61 | 62 |

BRIEF DESCRIPTION OF THE DRAWINGS

The accompanying colored photographic illustrations show the overall appearance and distinct characteristics of the new cultivar of *Vaccinium corymbosum* 'TH-1797' showing the colors as true as possible. Colors in the photographs may differ slightly from the color values cited in the detailed botanical description, which accurately describes the colors of the new *Vaccinium corymbosum* 'TH-1797'. Unless indicated otherwise, the photographs were taken of plants grown outdoors in Alapaha, Ga. taken in 2019 and 2020.

The photograph labeled

The photograph labeled

The photograph labeled

The photograph labeled

The photographs labeled

The photograph labeled

DETAILED BOTANICAL DESCRIPTION

Figure 1:
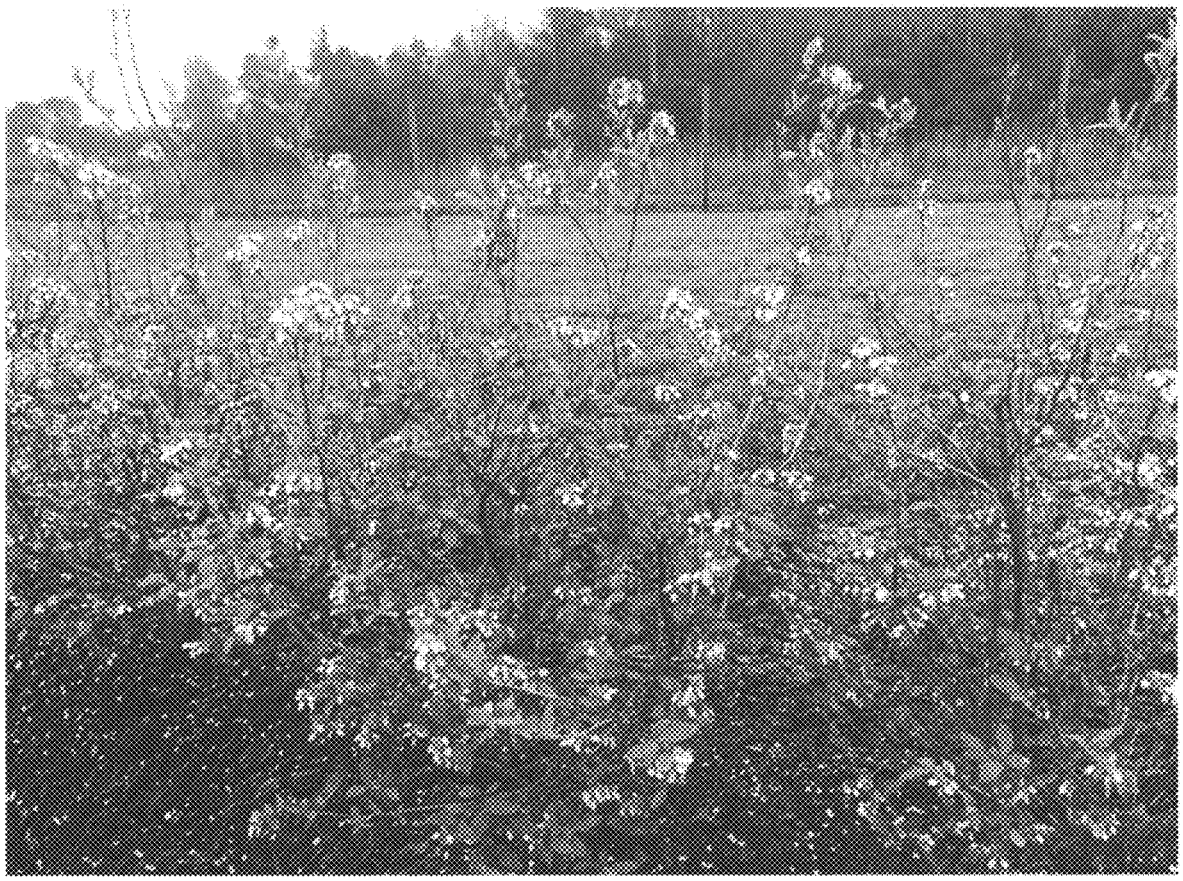
FIG. 1 depicts typical three-year old 'TH-1797' plants during flowering, taken in February 2020.
Figure 2:
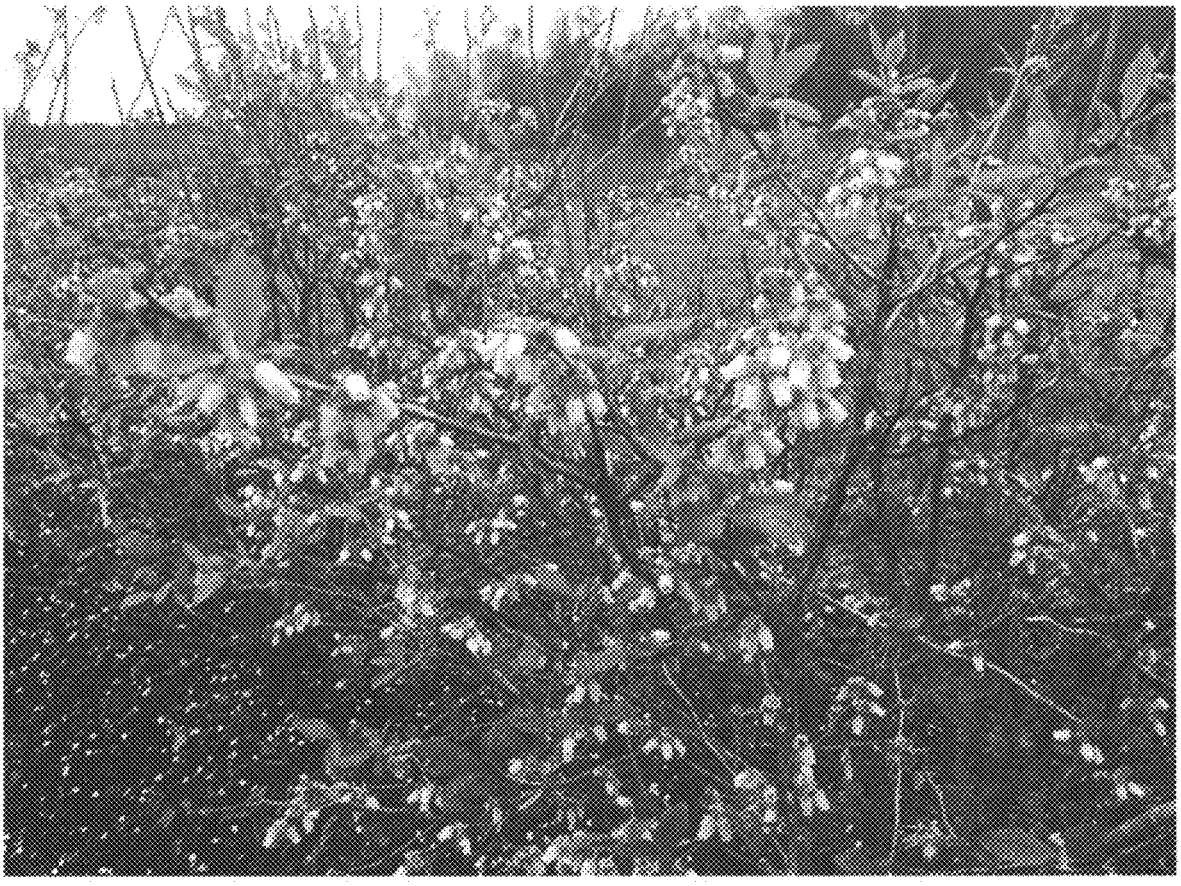
FIG. 2 depicts a close-up view of flowering branches of a 'TH-1797' plant.
Figure 3:
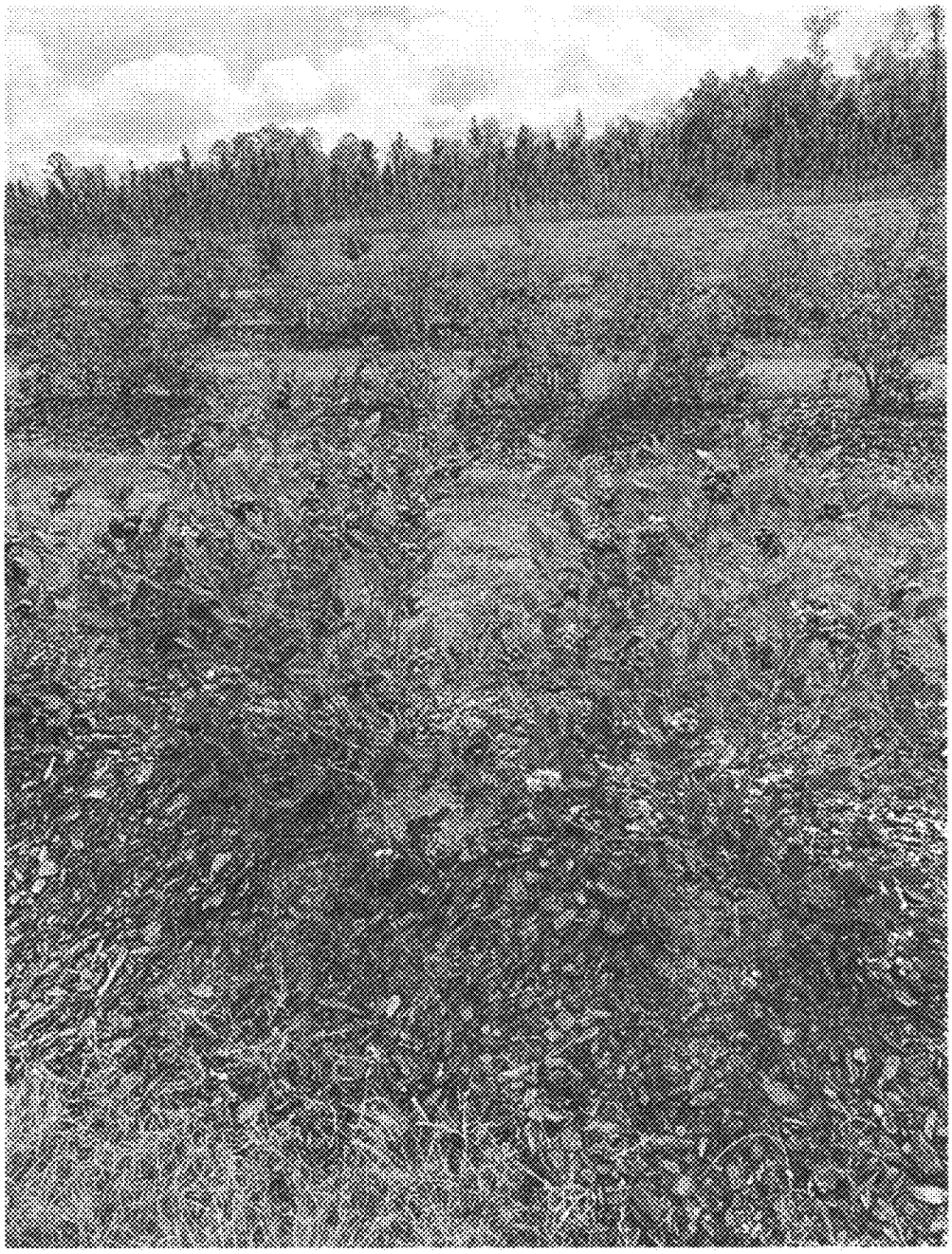
FIG. 3 depicts typical two-year old plants of 'TH-1797' during fruit ripening, taken in April 2019.
Figure 4:
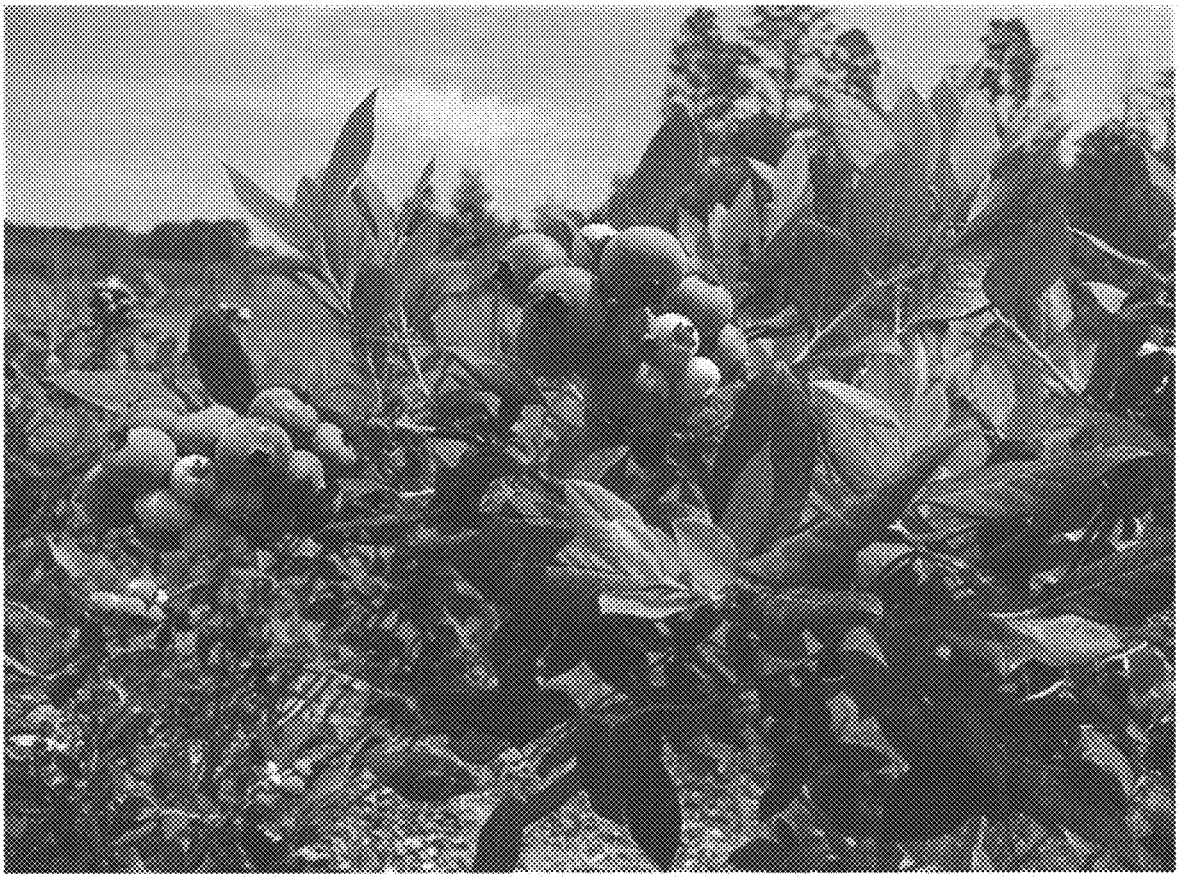
FIG. 4 depicts close-up view of maturing fruit of 'TH-1797', taken in April 2019.
Figure 5A:
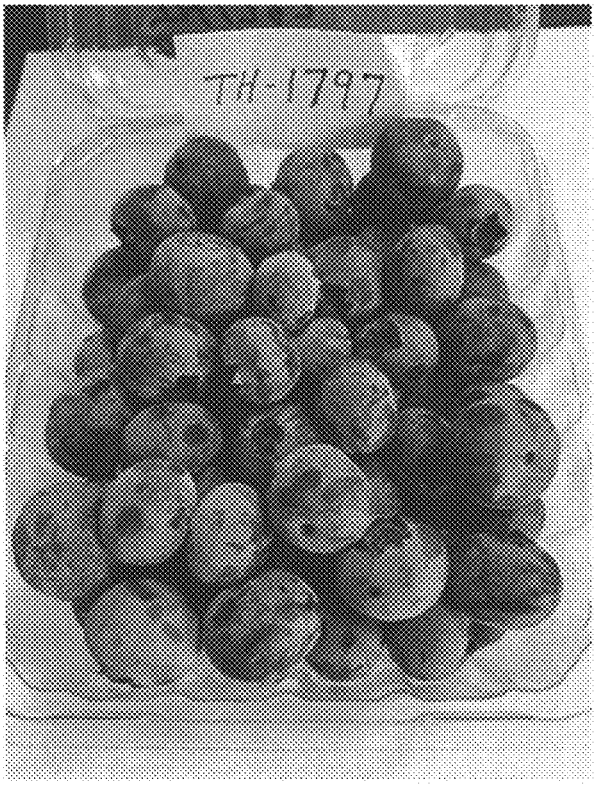
FIG. 5A and FIG. 5B are close-up views of ripe fruit of 'TH-1797', with FIG. 5B depicting two sliced berries to reveal the inside of the fruit. Photos taken in April 2020.
Figure 5B:
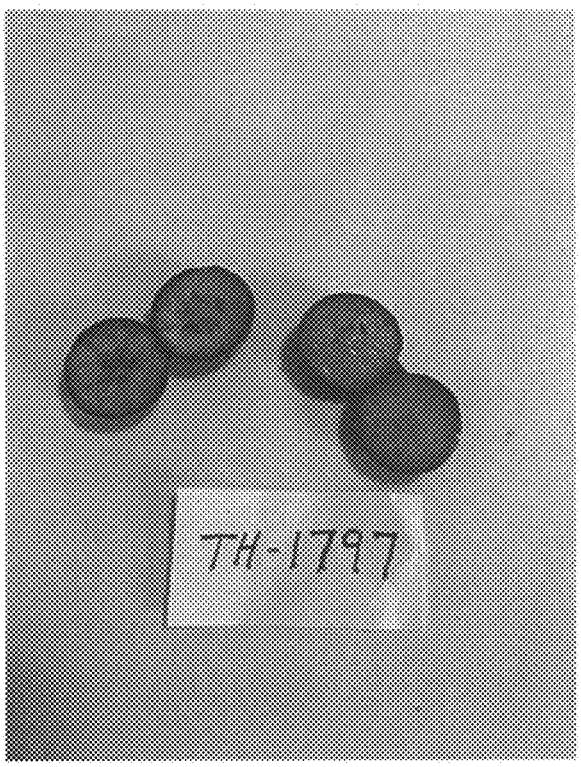
Figure 6:
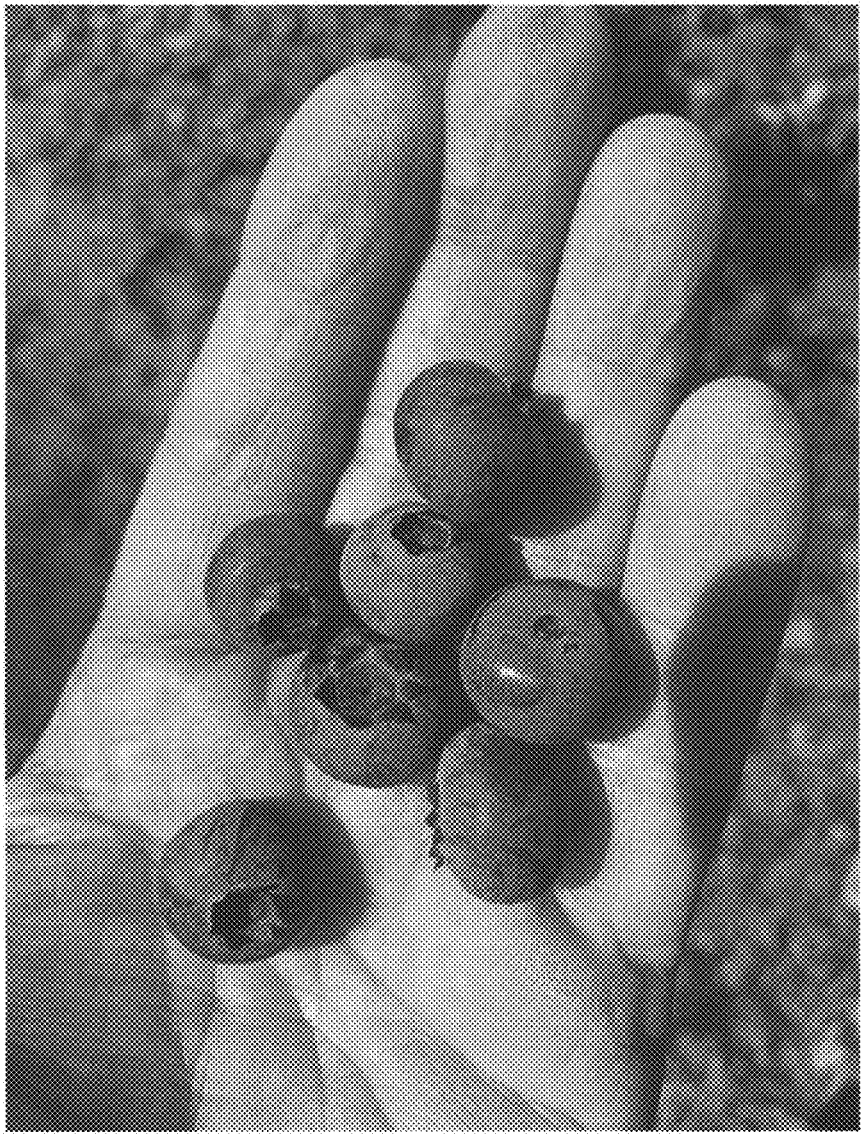
FIG. 6 is another close-up view of ripe fruit of 'TH-1797', in a human hand, illustrating the relative size of the fruit. Photo taken in April 2020.

The following traits have been consistently observed in the original plant of this new variety and in asexually propagated progeny grown in Alapaha, Ga., and, to the best knowledge of the inventors, their combination forms the unique characteristics of the new variety *Vaccinium corymbosum* 'TH-1797'.

Throughout this specification, color names beginning with a small letter signify that the name of that color, as used in common speech, is aptly descriptive. Color names beginning with a capital letter designate values based upon The R.H.S. Colour Chart, $5^{th}$ edition published by the Royal Horticultural Society, London, England in 2007, except where general terms of ordinary dictionary significance are used.

The aforementioned photographs and following observations, measurements, and values describe plants of the *Vaccinium corymbosum* cultivar named 'TH-1797'. Data were collected between the years of 2016-2020 from a horticulture farm and nursery in Alapaha, Ga. from 2 to 4-year-old plants (planted in the field with supplemental irrigation). The average low temperature for the year ranges from about 54° F. to 58° F., and the average high temperature for the year ranges from about 78° F. to 82° F.

Botanical classification: *Vaccinium corymbosum* 'TH-1797'.

*Commercial classification*.—Fruit-bearing shrub.

*Parentage*.—'TH-1120' X 'Suziblue' (U.S. Plant Pat. No. 21,167).

Growth and propagation:

*Propagation type*.—Vegetative by softwood cuttings.

*Growth rate*.—Moderately vigorous.

*Root description*.—Fibrous.

Plant description:

*Growth habit*.—Plant is mostly upright, with about 3 to 4 main canes arising from the original crown, and multiple branching of shoots from those canes about 15 to 20 cm above ground. Over time, numerous suckers (about 5 to 10) can emerge within about 10-15 cm of the original crown.

*Usage*.—Commercial and private fruit production.

*Productivity*.—High yielding. Yields of about 7 to 10 lbs fruit per plant each year on plants 4 years old or older grown under well fertilized and irrigated field conditions. Frost protection may be useful to reach yield potential due to early flowering.

*Size of plant*.—Plant is about 1.2 to 1.5 m tall by 3 to 4 years. Plants grown under highly productive soil and fertility conditions may exceed about 1.5 m tall in 4 years. The plant crown, or base, is typically about 20-30 cm in diameter. Upper portion of plant canopy reaches about 1.2 to 1.5 m in diameter by 3 to 4 years.

*Cold hardiness*.—Similar to other early ripening southern highbush varieties such as 'Suziblue' (U.S. Plant Pat. No. 21,167) and 'Rebel' (U.S. Plant Pat. No. 18,138).

*Disease resistance*.—No notable disease resistance or susceptibility observed. Estimated to be similar to other early season southern highbush such as 'Suziblue' and 'Rebel'.

*Chilling requirement*.—Plants are low to medium chill, requiring only about 200 to 300 hours, more or less, of temperatures at or below about 7° C. to induce normal leafing and flowering during the spring under conventional dormant production systems. The chill requirement is slightly less than the male parent 'Suziblue' (250 to 350 hours of chilling required), and considerably less than the female parent 'TH-1120' (non-patented breeding selection; 400 to 500 hours of chilling required).

*Leafing*.—Plants tend to break sufficient leaf buds simultaneously with, or shortly after, anthesis.

*Canes*.—Main cane base diameter about 20 to 30 mm, color most near Grey 201C; two year old cane diameter about 10 to 15 mm, color transitioning from Greyed Orange 166B to Grey 201C; current season wood diameter about 5 to 10 mm, color Yellow Green 145C.

*Fruiting wood*.—Moderate number of twigs (about 4 to 8 common) of about 10 to 15 cm in length, with internode lengths of about 10 to 15 mm common.

Foliage:

*Leaf color healthy mature leaves*.—Top side of leaf color is Green 137A, under side of leaf color is Green 138B.

*Leaf arrangement*.—Alternate, simple.

*Leaf shape*.—Elliptic.

*Leaf margins*.—Entire.

*Leaf venation*.—Pinnate with slight netting.

*Leaf apices*.—Broadly acuminate to broadly acute.

*Leaf bases*.—Acute.

*Leaf dimensions*.—Length: about 60 to 70 mm; width: about 30 to 40 mm.

*Petioles*.—Small, about 3.0 to 4.5 mm long, about 1.5 to 2.0 mm wide; Color: Green 139D.

*Texture*.—Leaf margins, smooth; both upper and lower leaf surfaces, glaucous.

Flowers:

*Date of* 50% *anthesis*.—3-year average around February 22 in southeast Georgia.

*Flower shape*.—Urceolate.

*Flower bud number*.—High, averaging about 3 to 6 buds per fruiting shoot.

*Flowers per cluster*.—About 4 to 7 common.

*Flower fragrance*.—None detected.

*Corolla color*.—White NN 155C.

*Corolla length*.—About 8.5 to 9.5 mm.

*Corolla width*.—About 7.5 to 8.5 mm.

*Corolla aperture width*.—About 4.5 to 5.5 mm.

*Flower peduncle*.—Length about 8.0 to 12.0 mm; Color: Green 138D.

*Flower pedicel*.—Length about 4.0 to 5.0 mm; Color: Green 138D.

*Calyx* (*with sepals*).—Diameter: about 7.5 to 9.0 mm; Color: sepals Green 138D; calyx center Green 138C.

*Stamen*.—Length: about 5.0 to 7.0 mm; number per flower: about 10; filament color: Green White 157C.

*Style*.—Length: about 8.0 to 9.0 mm; Color: Yellow Green 145B to 145C.

*Pistil*.—Length: about 9.5 to 10.5 mm; ovary color: Green 138D.

*Anther*.—Length: about 3.0 to 4.0 mm; number: 10; Color: Greyed Orange 165B.

*Pollen*.—Abundance: medium; Color: Yellow White 158B.

*Compatibility*.—The cultivar has a moderate degree of self-compatibility.

Fruit:

*Date of* 50% *maturity*.—3-year average around April 24 in southeast Georgia.

*Fruit development period*.—About 62 days in southeast Georgia.

*Berry color*.—With wax Violet Blue 98D; with wax removed Black 203A.

*Berry flesh color*.—White 155C.

*Berry surface wax abundance*.—High.

*Berry weight*.—$1^{st}$ harvest: about 3.5 to 4.1 g; $2^{nd}$ harvest: about 2.8 to 3.4 g.

*Berry size*.—Height from calyx to scar: about 15 to 17 mm; diameter: about 18 to 21 mm.

*Berry shape*.—Nearly spherical to slight disk shape.

*Fruit stem scar*.—Small to medium, dry, with no tearing upon harvest.

*Calyx*.—Depth shallow, less than about 1.0 to 1.5 mm; width medium, about 6.0 to 8.0 mm; sepals often present, semi-erect or outward when present, about 1.0 to 1.5 mm.

*Berry firmness*.—Good.

*Berry flavor and texture*.—Sweet, mildly acidic flavor; smooth texture.

*Storage quality*.—Very good.

*Suitability for mechanical harvesting*.—Likely suitable.

*Uses*.—Primarily to be used as fresh fruit for shipping and processing markets.

Seed:

*Seed abundance in fruit*.—Medium, about 10 to 20 fully developed seeds per berry.

*Seed color*.—Greyed Orange 165B.

*Seed dry weight*.—About 27.8 mg per 100 seed.

*Seed size*.—About 1.0 to 1.5 mm long.

It is claimed:

1. A new and distinct cultivar of the *Vaccinium* plant named 'TH-1797' as illustrated and described herein.

* * * * *